United States Patent [19]

Langer et al.

[11] Patent Number: 5,258,554
[45] Date of Patent: Nov. 2, 1993

[54] PROCESS FOR MONOBENZYLATION OF P-SUBSTITUTED PHENOLS

[75] Inventors: Reinhard Langer; Hans-Josef Buysch, both of Krefeld, Fed. Rep. of Germany

[73] Assignee: Bayer Aktiengesellschaft, Leverkusen, Fed. Rep. of Germany

[21] Appl. No.: 960,999

[22] Filed: Oct. 14, 1992

[30] Foreign Application Priority Data

Oct. 24, 1991 [DE] Fed. Rep. of Germany ....... 4135073
Nov. 28, 1991 [DE] Fed. Rep. of Germany ....... 4139053

[51] Int. Cl.$^5$ .............................................. C07C 39/14
[52] U.S. Cl. ..................................... 568/745; 568/744
[58] Field of Search ............... 568/650, 744, 745, 628, 568/58

[56] References Cited

U.S. PATENT DOCUMENTS

| | | | |
|---|---|---|---|
| 1,880,566 | 10/1932 | Weiler et al. | 568/745 |
| 2,769,844 | 11/1956 | Joris | 568/744 |
| 4,105,699 | 8/1978 | Starks | 568/744 |
| 4,661,645 | 4/1987 | Lee et al. | 568/744 |
| 5,041,692 | 8/1991 | Ungarelli et al. | 568/744 |
| 5,072,017 | 12/1991 | Buysch et al. | |
| 5,091,058 | 2/1992 | Davie et al. | 568/744 |

FOREIGN PATENT DOCUMENTS

| | | | |
|---|---|---|---|
| 0003338 | 8/1979 | European Pat. Off. | |
| 0278211 | 8/1990 | European Pat. Off. | |
| 185928 | 10/1966 | U.S.S.R. | 568/744 |
| 346298 | 8/1972 | U.S.S.R. | 568/744 |
| 916506 | 1/1963 | United Kingdom | 568/745 |

OTHER PUBLICATIONS

R. C. Huston, "Action of Aromatic Alcohols on Aromatic Compounds in the Presence of Aluminum Chloride," Jun., 1931, pp. 2379-2382.
J. Blackwell, "Alkylation of the Aromatic Nucleus," in *Soc.*, 1963, pp. 366-373.
Chemical Abstracts, vol. 79, 1973, p. 42071.
Chemical Abstracts, vol. 89, 1978, p. 6120, 89: 6109b.
Chemical Abstracts vol. 78, 1973, p. 438, 110754s.
No. 18265f, Abdurasuleva et al, "Alkylation of phenols and their ethers...", Chem. Abstr. vol. 79, (Jul. 1973), p. 416.
No. 5000p, Ismailov et al, "Benzylation of cresols," Chem. Abstr. vol. 91, (Jul. 1979), p. 469.

*Primary Examiner*—Werren B. Lone
*Attorney, Agent, or Firm*—Sprung Horn Kramer & Woods

[57] ABSTRACT

The invention relates to a process for the preparation of p-substituted o-benzylphenols by reaction of p-substituted phenols with optionally substituted benzyl halides, benzyl esters, benzyl alcohols or benzyl ethers in the presence of an acid catalyst at elevated temperature in a distillation column.

20 Claims, No Drawings

PROCESS FOR MONOBENZYLATION OF P-SUBSTITUTED PHENOLS

BACKGROUND OF THE INVENTION

The invention relates to a process for the benzylation of p-substituted phenols in the o-position.

It is known that mixtures of 2-benzyl-, 4-benzyl- and 2,6-dibenzyl-phenols and higher-boiling condensation products are always obtained in varying composition during the benzylation of phenols.

It is thus known, for example, from J. Amer. Chem. Soc. 53, 2379 (1931) that a product mixture which, depending on the ratio of the amounts of the starting substances, contains 30 to 36% by weight of dibenzylated secondary and side reaction products is formed in the condensation of p-cresol with benzyl alcohol in the presence of aluminium chloride.

It is furthermore known [Abdurasuleva et al., Zh. Org. Khim. 9, 132 (1973)] that up to 18 mol % of dibenzyl chlorophenols are formed in the benzylation of 4-chlorophenols with benzyl chloride in the presence of catalysts such as $FeCl_3$, $FeSO_4$ or $ZnSO_4$. Moreover, the condensation of 4-chlorophenol with benzyl chloride in a molar ratio of 4:1 in the presence of 10% by weight of a sulphonated styrene/divinylbenzene copolymer (strongly acid cation exchanger) to give 2-benzyl-4-chlorophenol is described in Czech Patent Specification 170,972 [Chemical Abstracts 89, (1978), 6109 b]. The yield of the desired product is indeed 83%, based on the 4-chlorophenol reacted; however, a relatively large amount of higher-boiling secondary and side reaction products is also formed; the ratio of the 2-benzyl-4-chlorophenol formed to the higher-boiling products is 4.16:1.

As well as having a low selectivity and therefore a low utilisation of the starting materials, the processes described require a large excess of phenol and long reaction times because of a slow introduction of the benzylating agent and an after-reaction period (for example 3+2=5 hours in CS 170,972), which means that a low space/time yield is achieved Furthermore, a large amount of catalyst has to be separated off and regenerated or destroyed.

Zeolites of the faujasite type are described in EP 278,211 as catalysts for the reaction of p-substituted phenols with optionally substituted benzylating agents. Using 10% by weight of Na-Y as the catalyst, 1 mol of benzyl alcohol can be reacted quantitatively with 4 mol of 4-chlorophenol within 3 hours at 200° C., the ratio of 2-benzyl-4-chlorophenol formed to higher-boiling products of 9.9:1 being significantlly better than that in CS 170,972. However, the removal and, where appropriate, regeneration of the catalyst employed is technically cumbersome.

SUMMARY OF THE INVENTION

It has now been found that the desired monobenzylation of p-substituted phenols in the o-position can be achieved with a high space/time yield and a high selectivity in a completely continuous process if the p-substituted phenols are reacted with optionally substituted benzyl halides, benzyl esters, benzyl alcohols or benzyl ethers or mixtures of these halides, esters, alcohols and ethers in a distillation apparatus in the presence of at least one soluble acid catalyst.

The invention therefore relates to a process for the preparation of o-benzylphenols substituted in the p-position, of the formula

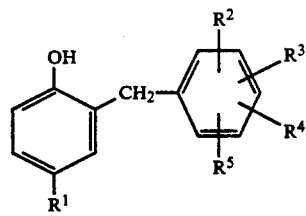
(I)

in which
$R^1$ represents halogen, hydroxyl, $C_1$-$C_{12}$-alkyl, $C_1$-$C_{12}$-alkoxy, $C_1$-$C_{12}$-alkylmercapto, $C_6$-$C_{12}$-aryl, $C_6$-$C_{12}$-aryloxy or $C_6$-$C_{12}$-arylmercapto and
$R^2$ to $R^5$ independently of one another denote hydrogen, halogen, the cyano group, $C_1$-$C_{12}$-alkyl, $C_1$-$C_{12}$-alkoxy, $C_1$-$C_{12}$-alkylmercapto, $C_6$-$C_{12}$-aryl, $C_6$-$C_{12}$-aryloxy or $C_6$-$C_{12}$-arylmercapto, and two of radicals $R^2$ to $R^5$, if they are adjacent, denote trimethylene, tetramethylene or the radical of a fused-on benzene ring, by reaction of p-substituted phenols of the formula

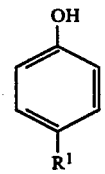
(II)

in which
$R^1$ has the abovementioned meaning,
with benzyl compounds of the formula

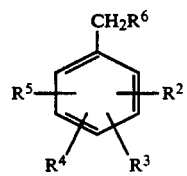
(III)

in which
$R^2$ to $R^5$ have the abovementioned meaning and
$R^6$ represents halogen, $C_1$-$C_{12}$-alkylcarboxyl, substituted or unsubstituted phenylcarboxyl, $C_1$-$C_{12}$-alkyl- or phenylsulphatoxy, hydroxyl, $C_1$-$C_{12}$-alkoxy, substituted or unsubstituted benzyloxy or substituted or unsubstituted p-$R^1$-phenoxy, wherein $R^1$ has the abovementioned meaning,
which is characterised in that the reaction is carried out in a continuously operating distillation apparatus in the presence of at least one acid, soluble catalyst.

The course of the reaction can be represented as follows:

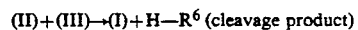

(II)+(III)→(I)+H—$R^6$ (cleavage product)

DETAILED DESCRIPTION OF THE INVENTION

Possible alkyl radicals of the abovementioned formulae, including in the alkoxy substituents, are those having 1 to 12, preferably 1 to 4, carbon atoms, which can be straight-chain or branched. Examples which are mentioned are: methyl, ethyl, n-propyl, iso-propyl, n-butyl, isobutyl, sec-butyl, tert-butyl, pentyl, hexyl, octyl, decyl and dodecyl, preferably methyl, ethyl, n-propyl, isopropyl, n-butyl, iso-butyl, sec-butyl and tert-butyl, particularly preferably methyl.

Halogen which may be mentioned is: fluorine, chlorine, bromine and iodine, preferably fluorine, chlorine and bromine, particularly preferably chlorine and bromine, especially preferably chlorine.

Alkyl, alkoxy, phenyl and benzyl can be mono- or disubstituted by methyl, ethyl, methoxy, ethoxy or chlorine.

Preferred p-substituted phenols for the process according to the invention are those of the formula

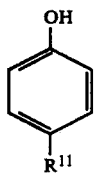

(IV)

in which
$R^{11}$ represents fluorine, chlorine, bromine, hydroxyl, $C_1$-$C_4$-alkyl, $C_1$-$C_4$-alkoxy, phenyl or phenoxy.

Particularly preferred p-substituted phenols for the process according to the invention are those of the formula

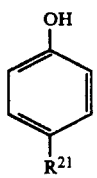

(V)

in which
$R^{21}$ represents chlorine, bromine, hydroxyl, methyl or methoxy.

Preferred benzyl compounds of the formula (III) are those in which $R^5$ represents hydrogen. Particularly preferred benzyl compounds of the formula (III) are those in which $R^4$ and $R^5$ represent hydrogen.

The following p-substituted phenols, for example, can be employed for the process according to the invention: p-chlorophenol, p-cresol, hydroquinone monoethyl ether, p-bromophenol, p-hydroxybiphenyl, 4-chloro-4'-hydroxybiphenyl and p-fluorophenol, preferably p-chlorophenol, p-cresol and hydroquinone monoethyl ether, particularly preferably p-chlorophenol and p-cresol.

Possible benzylating agents are, for example: benzyl chloride, benzyl bromide, benzyl acetate, benzyl formate, benzyl trichloroacetate, benzyl valerate, dibenzyl sulphate, benzyl mesylate, benzyl alcohol, dibenzyl ether, p-chlorophenyl benzyl ether, p-methylbenzyl alcohol, bis-p-methyl-benzyl ether, p-hydroxymethylchlorobenzene and bis-p-chloro-benzyl ether, preferably benzyl chloride, benzyl alcohol, the dibenzyl ethers and p-chlorophenyl benzyl ether.

According to the invention, the phenols and the equivalents of benzylating agent are reacted in a molar ratio of greater than 2, preferably greater than 4, particularly preferably greater than 8, especially preferably greater than 12, the upper limit of the molar ratios being 50, preferably 40, particularly preferably 30. However, in the process according to the invention, this excess phenol occurs exclusively within the continuously operating reactor and is reflected in the selectivity achieved.

It is a particular advantage in the process according to the invention that the educts are metered into the reactor in approximately equimolar amounts and the products are removed from the reactor at separate points in pure or prepurified form, but, the reaction proceeds with a desired greater or smaller excess of phenol which can be adjusted in a controlled manner.

The process according to the invention is carried out in a continuously operating distillation apparatus in which the pressure and reaction temperature are linked to one another to the extent that the boiling points and therefore the temperature profile in the distillation column are determined by the pressure applied.

In the simplest case, the apparatus for carrying out the process according to the invention consists of an isolated column, charged with filling bodies or with a distillation packing, for carrying out a continuous distillation, as is the prior art.

Such an apparatus has, in general, a heat exchanger at the foot of the column and a condenser with a reflux divider at the column head. The product, if appropriate together with dibenzylated and more highly benzylated byproducts, is discharged at the foot of the column. One possible procedure comprises removing the product (I) in a form free from high-boiling constituents from the lower part of the column in a side stream and in this way isolating it in the pure form; the product-free highboiling constituents are then removed at the foot of the column.

The column is advantageously provided with an additional heat exchanger above the zone, for discharge of the product.

This heat exchanger is charged with all or with a part stream of the reacted reaction mixture flowing out, and serves to evaporate the majority of the excess phenol (II) "confined" in the column, to release the lower distillation region for purifying distillation or partial purification of the product.

The column is furthermore advantageously provided with another, additional heat exchanger below the column head. This serves to precipitate the majority of the phenol content of the gas phase flowing to it, preferably with recovery of energy, for example by steam generation, in order to release the upper part of the column for separation of the low-boiling reaction product from the excess phenol. The column can therefore be divided into three zones, with or without additional heat exchangers, into the upper zone for separation of the low-boiling cleavage product H—$R^6$ from the excess phenol, into the lower part for separation of the product from the excess phenol (II) and if appropriate from high-boiling by-products, and into the central part in which (overlapping with the distillation operation) the reaction (II+III→I+ H—$R^6$) proceeds. All three zones have, where appropriate, different column packings and column diameters according to their liquid and gas load. If appropriate, a distillation apparatus in the above sense can also consist of several distillation columns connected in series with pipelines for the vapours and streams of liquid.

The filling bodies or ordered packings to be used are those customary for distillations, such as are described, for example, in Ullmanns Encyclopädie der Techn.

Chemie (Ullmann's Encyclopaedia of Industrial Chemistry) Volume 2, page 528 et seq. (4th edition) or in company publications, for example from Sulzer, Montz, Raschig, Kühni or Norton.

Examples which may be mentioned are: Raschig ® or Pall ® rings, Berl-Intalex or Torus ® saddles, and interpacking bodies of various materials, such as glass, stoneware, porcelain, carbon, stainless steel and plastic, which can be processed (especially as metal) in a fabric- or mesh-like form.

Filling bodies and ordered packings which have a high surface area and display good wetting as well as an adequate residence time of the liquid are preferred, for example Pall ® and Novolax ® rings, Berl saddles, BX ®. packings, Montz-Pak ®, Mellapak ®, Melladur ®, Kerapak ® and CY ® packings.

However, not only packed columns but also those with fixed baffles are suitable for the process according to the invention. Tray columns having perforated, bubble, valve, tunnel and centrifugal trays, which in turn can be present in various embodiments, are suitable. Bubble and valve trays having high residence times and a good exchange of matter, for example, are preferred.

In the embodiment with two additional heat exchangers which frame the reaction part of the column, the reaction part preferably has a larger diameter than the other column sections.

The cross-sectional area of the reaction part is preferably more than twice, particularly preferably more than three times, especially preferably more than four times as large as that of the lower column section.

The three components: phenol (II), benzylating agent (III) and catalyst can be metered in separately, if appropriate at different points of the column, or as a mixture. Preferably, the catalyst is metered in with the phenol above the upper heat exchanger or the reaction zone, while the benzylating agent, depending on its relative volatility with respect to the phenol (II), is metered in directly below the upper heat exchanger or in the upper third, in the centre or in the middle third or at the lower end or in the lower third of the reaction part, depending on whether it has a low, moderate or high volatility.

The feed point is chosen so that as far as possible no benzylic starting material or intermediate product leaves the reaction region unreacted; this particularly applies in the direction of the lower column part. The optimum point depends on the relative volatility of the phenol (II) and benzylating agent (III), and can be determined easily for each specific case by simple experiments and calculations. If a particularly highly volatile benzylating agent leaves the reaction region in the direction of the column head to a relatively large extent, it can easily be removed from the upper column part, if appropriate as a mixture with phenol which is not separated off, and recycled to the lower part of the reaction region of the column together with fresh benzylating agent.

An additional azeotrope-forming agent can in principle be fed into the column at any point, and is preferably metered in as a mixture with the phenol and the acid catalyst.

It serves to separate the low-boiling cleavage product H—$R^6$ from the phenol (II) as easily and completely as possible in the upper part of the column.

This particularly applies if benzyl alcohol or dibenzyl ether is used as the benzylating agent and the phenol (II) to be benzylated forms an azeotrope and is miscible in all proportions with water.

Such azeotrope-forming agents are known to the expert, and examples which may be mentioned are: benzene, toluene, o-xylene, p-xylene, chlorobenzene, butanol, hexanol, diethyl ether, dibutyl ether and carbon tetrachloride. The procedures for separation of azeotropic mixtures by distillation by means of auxiliary components are summarised as a review and illustrated by examples in Chem. Eng. Prog. 85, 63–69 (1989).

The molar metering ratio of phenol to benzylating component (in benzyl units) must be varied slightly according to the discharge of phenol and benzyl via the head of the distillation column and according to the additional benzyl consumption by formation of high-boiling byproducts, in order to maintain the internal excess of phenol. It is in general 2:1 to 1:2, preferably 1.5:1 to 1:1.5, particularly preferably 1.1:1 to 1:1.1.

The amounts of phenol, benzylating agent and azeotropeforming agent distilled off via the head can be recycled back to the distillation after removal of the low-boiling cleavage product.

The pressure range in which the process according to the invention is carried out is between 1 mbar and 10 bar, preferably between 10 mbar and 1 bar, particularly preferably between 20 mbar and 500 mbar.

The temperature in the reaction region of the column in the process according to the invention is between 100 and 240° C., preferably between 120 and 210° C., particularly preferably between 140 and 190° C., especially preferably between 160 and 180° C.

The temperature in the lower part of the column is above the temperature in the reaction part but below 350° C., preferably below 300° C., particularly preferably below 250° C.

The use of an acid soluble compound to accelerate the reaction in the process according to the invention is particularly advantageous. High reaction rates and, in the case of a stationary catalyst system, a stable heterogeneous contact are required for carrying out a reaction in a distillation column effectively. Although experiments carried out by the Applicant Company for benzylation of p-chlorophenol by means of benzyl alcohol or benzyl chloride under catalysis by stationary heterogeneous catalysts in a distillation column gave good conversions and selectivities, the service lives of the catalysts were only inadequate, which necessarily constantly causes interruptions in production and extensive cleaning and regenerating operations.

It has now been found that the use of dissolved acid catalysts ensures that the reaction corresponding to the process according to the invention is carried out in a trouble-free manner.

Friedel-Crafts catalysts can be employed as homogeneous catalysts. These are metal salts or complexes and mixtures of salts or complexes and their hydrates, phenolates, alcohols and acid adducts with cations of oxidation levels I, II, III, IV and V, such as have been listed, for example, by G.A. Olah in "Friedel-Crafts and Related Reactions" (Volume I, pages 284–290, pages 307–308 and pages 314–315), and which are less active in the Lewis and more active in the Brönsted acid form (pages (208–215).

Brönsted acids such as are listed, for example, by G.A. Olah on page 238 are preferably employed directly as catalysts. These are moderately strongly to strongly acid catalysts having $pK_a$ values of between plus 3 and minus 12 (in relation to water, measured in $H_2SO_4/H_2O$ mixtures).

J. Blackwell describes the procedure for the reaction between benzyl benzenesulphonate and phenol at 125° C. in the course of several hours (Soc. 1963, pages 366–73). In SU 333,863, benzyl alcohol is reacted with phenol in the presence of about 1.5% of hydrogen sulphates ($pK_a=$ 1.99, Bruckenstein and Kolthoff, "Treatise on Analytical Chemistry", Volume 1, part 1, pages 432–433) within several hours, water being removed. The reaction with 1 to 2 mol % of $NaHSO_4$ at 150° C. is described as the optimum in C.A. 79: 42079.

A.R. Abdurasaleva uses 10% by weight of $H_2SO_4$ ($pK_a=-9$, Bell, "The Proton in Chemistry", 2nd edition, Cornwell University Press, Ithaca, N.Y., 1973) or $H_3PO_4$ ($pK_a=$ 0.85) (Zh. Org. Khim., 8 (1972) pages 134–36, 7 (1971) pages 1001–3) at 100 to 160° C.

The use of amounts of catalyst of about 10% accordingly corresponds to the prior art and leads to the conclusion that the benzylation of phenols with benzyl alcohols or benzyl chlorides is only a moderately fast reaction which requires relatively large amounts of catalyst. There seems to be a tendency here to employ weaker acids, such as, for example, hydrogen sulphates. On the part of the heterogeneous catalysts, the use of Na-Y for the benzylation of p-substituted phenols corresponds to this (EP 278,211).

In the absence of catalysts, according to experiments carried out by the Applicant Company, no benzylation product is detected in a mixture of p-chlorophenol and benzyl alcohol even after 8 hours at 180° C. (Comparison Experiment 1).

For a reaction to be carried out effectively in a distillation column, it is desirable for reaction times in the region of significantly less than one hour, preferably a few minutes, to be realised.

On the basis of the above literature, it was to be expected that even larger amounts of catalyst than is described for the known batch process of low space/time yield and long residence time (reaction time) would be required for the process to be carried out according to the invention. Strongly acid catalysts in the context of the above list, such as are employed in the process according to the invention, are to be classified as being less advantageous according to the prior art corresponding to the above references (see the use of hydrogen sulphates and of Na-Y).

Surprisingly, it has been found that even small amounts of a strong acid having $pK_a$ values of 0 to $-12$ accelerate the desired phenol benzylation enormously.

The reaction between p-chlorophenol and benzyl alcohol has thus proceeded quantitatively within 15 minutes at 160° C. in the presence of, for example, 0.1–1 mol % of methanesulphonic acid, sulphuric acid, toluenesulphonic acid or benzenesulphonic acid, so that neither benzyl alcohol nor intermediate products, such as dibenzyl ether and p-chlorophenyl benzyl ether, can be detected.

Weaker acids, such as, for example, acetic acid and benzoic acid, must be employed in considerably larger amounts of at least 5 mol %, and even then achieve nowhere near the rate of catalysis of strong acids in the sense of the above definition.

This observation is of great importance specifically for the process according to the invention, since it is not necessary to circulate large amounts of catalyst in order to achieve the desired reaction rates, and reuse of the catalyst can even be dispensed with, if appropriate.

In a particular form of carrying out the process according to the invention, after leaving the reaction part, it can even be neutralised while still in the apparatus by feeding in an appropriate amount of a non-volatile base, in order to suppress any undesirable side reactions in the lower column part.

Accordingly, the process according to the invention is particularly preferably carried out in the presence of soluble Brönsted acids, the $pK_a$ value of which (measured in $H_2SO_4/H_2O$ mixtures, in relation to water) is between 0 and $-12$, preferably between $-1$ and $-12$, particularly preferably between $-2$ and $-12$.

The molar amount of acid, in relation to the benzyl equivalents metered in, is between 10 and 0.001 mol %, preferably between 5 and 0.002 mol %, particularly preferably between 1 and 0.004 mol %.

After passing through the reaction zone, in which it is concentrated or diluted to a greater or lesser degree, depending on its volatility, the catalyst enters the lower processing part of the apparatus, where it can give rise to decomposition reactions, especially at very high temperatures, and contaminate the product.

If appropriate, the process according to the invention can therefore be modified by metering in a base or a buffer mixture below the reaction zone or the central heat exchanger and above the product withdrawal point, in order to neutralise the product stream flowing down.

After admixing with the base, the pH of the product stream should be greater than 2, preferably greater than 3, particularly preferably greater than 4. Suitable bases (or buffer systems) are non-volatile inorganic and organic bases, such as, for example, phenolates, carbonates, hydrogen carbonates, carboxylates, alcoholates, phosphates, hydrogen phosphates, dihydrogen phosphates, sulphates and hydroxides or oxides of alkali metals and alkaline earth metals.

The metering in of the base is carried out in parallel with the metering in of the acid and can be measured and controlled by known methods.

The selectivities which can be achieved in the process according to the invention depend on the internal excess of phenol and are in general above 90% of theory.

The process according to the invention represents a significant advance in comparison with the prior art, because it opens up a selective continuous access to o-benzylated, p-substituted phenols with a simple apparatus, good utilisation of energy and substances and a high space/time yield.

The fact that only very small amounts of a strong acid are required in the process according to the invention represents a further significant advance. p-Substituted o-benzylphenols are known compounds and are employed, according to German Offenlegungsschrift 2,211,266 and U.S. Patent Specification 4,514,577, as antioxidants and bactericides.

EXAMPLES

EXAMPLE 1 (Comparison Example)

Stirring experiment, no catalyst 3000 g of a mixture of p-chlorophenol and benzyl alcohol (molar ratio of 5 to 1) were introduced onto a 10 cm high column of $KHCO_3$ ($\phi=3$ cm) at room temperature in the course of 30 minutes. The acid-free starting material mixture thus obtained was kept under a nitrogen atmosphere.

100 g of the starting material mixture were heated to 180° C. under nitrogen. After 8 hours, a small sample was removed and a gas chromatography analysis was carried out. No product or intermediate product was detectable. (Detection limit about 0.01 per cent by weight)

EXAMPLE 2

Stirring experiments, various acid catalysts 100 g of the starting material mixture prepared over $KHCO_3$ in Example 1 were mixed with 0.1, 1 or 5 mol % (based on the sum of the molar amounts of phenol and benzyl alcohol) of an acid and the mixture was heated to 160° C. under a gentle stream of nitrogen. The content of 2-benzyl-4-chlorphelol in percentage area is shown as a function of time in Table 1.

column part thermostatically controlled by oil and containing porecelain saddles (diameter about 2.7 cm, height about 15 cm);
air bridge to downwards-operated condensation part of two intensive condensers, Anschütz head, vacuum bleeder connection and gas cap with vacuum hose.

The vacuum in the apparatus was kept constant by a magnetically controlled water pump ($\pm 1.5$ mbar).

The starting material mixture was metered in using a vacuum-tight metering pump (TELAB, PTFE minimeterer). The three thermostatically controlled column regions were heated or cooled by means of oil thermo-

TABLE 1

Formation of 2-benzyl-4-chlorophenol as a function of the acid content and time (content in % area).
$pK_a$ values of the acids, where stated, according to E. P. Serjeant and B. Dempsey, "Ionisation Constants of Organic Acids in Aqueous Solution", Pergamon, New York 1979.

| Time minutes | mol % | A | B | C | D | E | F | G | H | I | J | K | L |
|---|---|---|---|---|---|---|---|---|---|---|---|---|---|
| 5 | 0.1 | 0 | 0 | 0 | 0.0 | 0 | 0 | 0 | 0 | 0 | 0 | 0 | 0 |
|  | 1 | 0 | 1.2 | 0 | 22.7 | 0 | 23.5 | 0 | 0 | 0 | 0.1 | 21.0 | — |
|  | 5 | 0 | 7.1 | 0 | 22.7 | 0 | 23.6 | 0 | 1.0 | 1.2 | 3.2 | 22.3 | 2.7 |
| 15 | 0.1 | 0 | 0 | 0 | 0.0 | 0 | 0 | 0 | 0 | 0 | 0 | 0 | 0 |
|  | 1 | 0 | 3.5 | 0 | 20.7 | 0 | 23.4 | 0 | 0 | 0 | 0.2 | 21.1 | — |
|  | 5 | 0 | 12.8 | 0 | 22.8 | 0 | 23.6 | 0 | 4.2 | 4.9 | 6.6 | 21.8 | 10.1 |
| 60 | 0.1 | 0 | 0 | 0 | 0.0 | 0 | 0 | 0 | 0 | 0 | 0 | 0 | 0 |
|  | 1 | 0 | 13.6 | 0 | 22.7 | 0 | 23.4 | 0 | 0 | 0 | 2.9 | 21.1 | — |
|  | 5 | 0 | 22.5 | 0 | 22.9 | 0 | 23.6 | 0 | 15.8 | 16.7 | 14.9 | 21.8 | 20.7 |
| 120 | 0.1 | 0 | 0 | 0 | 0.0 | 0 | 0 | 0 | 0 | 0 | 0 | 0 | 0 |
|  | 1 | 0 | 22.8 | 0 | 22.8 | 0 | 23.4 | 0 | 0 | 0 | 22.1 | 21.2 | — |
|  | 5 | 0 | 22.4 | 0 | 22.8 | 0 | 23.5 | 0 | 21.7 | 21.6 | 21.5 | 21.8 | 21.2 |

22–24% of 2-benzyl-4-chlorophenol corresponds to 100% conversion
A = no acid ($pK_a$ = —)
B = oxalic acid (1.0–1.295)
C = acetic acid (4.48–4.76)
D = methanesulphonic acid (−1.2 to −1.86)
E = benzoic acid (4.205)
F = benzenesulphonic acid (—)
G = pivalic acid (—)
H = trifluoroacetic acid (0.50–0.52)
I = trichloroacetic acid (0.517–0.538)
J = chlorodifluoroacetic acid (—)
K = sulphuric acid (—)
L = phosphoric acid (—)

EXAMPLE 3 (Comparison Example)

Reaction distillation, catalyst zeolite Na-Y, educts: benzyl alcohol, p-chlorophenol The apparatus consisted of, from the bottom upwards:
glass flask (250 ml) having a regulated nitrogen inlet for receiving the bottom product (the main product of the reaction is obtained from this flask by being suctioned off from time to time);
coil evaporator thermostatically controlled by oil (coil length about 1.50 m, internal diameter of tube about 1.5 cm);
vacuum-metallised packed column, filled with 0.5 cm of large porcelain saddles (internal diameter of the column about 2.7 cm, height of the column about 35 cm);
column part thermostatically controlled by oil, filled with porcelain saddles (diameter about 2.7 cm, height about 35 cm);
two packed columns (vacuum-metallised) containing catalyst (reaction part, diameter about 2.7 cm, height about 35 cm, overall height about 70 cm);
water-cooled metering point (the starting material mixture is cooled up to the drip opening to prevent premature reaction);

stats.

190 g of zeolite Na-Y (modulus=4.7), bonded with 30% of $Al_2O_3$ (Pural SCF) in the form of rods 0.5 to 2.5 cm long and having a diameter of 2–3 mm were introduced into the reaction part of the apparatus.

The pressure was adjusted to 120 mbar and pure p-chlorophenol was first introduced into the lower part of the apparatus from a heated dropping funnel until a clear reflux was established in the entire apparatus (oil temperature of the lower evaporator about 260° C., oil temperature of the middle evaporator about 170° C., oil temperature of the upper condenser about 50° C.). A stream of $N_2$ of 0.1 Nl/hour was introduced into the lower part of the apparatus. A mixture of 1.5 mol of p-chlorophenol and 1 mol of benzyl alcohol was now metered in (about 150 g/hour). During this, the temperature of the lower evaporator was raised until a temperature of about 190°–220° C. was measured at the end of the lower column. The temperature of the middle evaporator was raised until there was a significant jump in temperature between the lower end of the catalyst bed and the upper end of the lower column (from about 150° C. to about 170° C.). The temperature of the upper condenser remained set at 50° C. and was raised only if flooding of the column was threatened.

The temperature above the condenser (dephlegmator) varied between 120 and 140° C.

About 105 to 106 g of a mixture of 97.8% of 2-benzyl-4-chlorophenol, 0.8% of benzyl 4-chlorophenyl 1.4% of high-boiling constituents (polybenzylated phenols) per hour dripped into the bottom flask of the apparatus. After passing through the air bridge, 44–45 g of a mixture of water, benzyl alcohol and p-chlorophenol condensed in the condensation part of the apparatus. The ratio of benzyl alcohol to p-chlorophenol in the organic phase was 5.4% to 94.6%.

As the running time increased, the amount of condensate rose constantly, the benzyl alcohol content increasing, which is an indication of the progressive deactivation of the catalyst, which manifested itself in a dark brown discoloration of the catalyst particles.

The catalyst was almost completely deactivated after 100 hours.

EXAMPLE 4 (Comparison Example)

Reaction distillation, no catalyst, starting materials: benzyl chloride, p-chlorophenol In the apparatus described in Example 3, the catalyst was replaced by inert porcelain saddles. Benzyl chloride was metered in instead of benzyl alcohol, and the procedure was otherwise as in Example 3.

By far the majority of the starting material mixture distilled off in unreacted form. The bottom product consisted of 2-benzyl-4-chlorophenol and benzyl 4-chlorophenyl ether in a ratio of 0.7:1.

The content of high-boiling products in the bottom product was 7%.

EXAMPLE 5 (Comparison Example)

As Example 4, but with a counter-current of HCl

Example 5 differed from Example 4 in that 0.1 Nl of HCl gas/hour was metered into the lower flask. The result of the example corresponded to that in Example 4 without a counter-current of HCl.

EXAMPLE 6 (Comparison Example)

Reaction distillation, catalyst of acid laminar silicate, starting materials: benzyl chloride, p-chlorophenol In the apparatus described in Example 3, the catalyst was replaced by Raschig rings of K306 (acid laminar silicate from Südchemie). The procedure was otherwise as in Example 4.

The result corresponded to that of Example 4, but the product contained no benzyl 4-chlorophenyl ether and consisted of 2-benzyl-4-chlorophenol to the extent of 80% and of high-boiling constituents to the extent of 20%.

EXAMPLE 7(Comparison Example)

Similar to Example 6

Example 6 was repeated by feeding in the benzyl chloride separately from the p-chlorophenol 35 cm above the lower end of the catalyst.

Under a loading of about 106 g/hour of p-chlorophenol (pump and line heated) and about 90 g/hour of benzyl chloride, about 152 g/hour of a mixture of 95.2% of 2-benzyl-4-chlorophenol and 4% of high-boiling constituents were obtained. About 18 g/hour of p-chlorophenol were obtained as the distillate.

The catalyst was deactivated within 2 hours.

EXAMPLE 8

Reaction distillation, catalyst of methanesulphonic acid, starting materials: benzyl alcohol, p-chlorophenol In the apparatus described in Example 3, the catalyst was replaced by inert porcelain saddle supports. The apparatus was again started up initially with pure p-chlorophenol, as described, under 120 mbar, and a weak counter-current of $N_2$ was passed through (0.11 Nl/hour).

Pumping of about 100 g/hour of a mixture of 128.5 g of p-chlorophenol, 108 g of benzyl alcohol and 192 mg of methanesulphonic acid (0.1 mol %) into the apparatus via the cooled dropping finger was then started. The lower thermostat and the middle thermostat pumped oil in circulation at a temperature of 250° C. and the upper thermostat pumped oil at a temperature of 67° C.

A temperature of 190°–200° C. was established at the end of the bottom-most column, and a temperature jump from 152–154 to 165°–195° C. was measured at the middle evaporator.

About 84.1 to 89.8 g of a mixture of 92–97% by weight of 2-benzyl-4-chlorophenol, 1% of 3-benzyl-4-chlorophenol and 2–7% of high-boiling constituents per hour left the lower end of the apparatus. No benzyl 4-chlorophenyl ether was to be detected.

About 20.2 to 15.9 g of a mixture consisting of about 7.6 g of water and p-chlorophenol per hour were obtained at the column head.

Apart from slight variations caused by the apparatus, the reaction proceeded in a constant manner.

EXAMPLE 9

Reaction distillation, catalyst of methanesulphonic acid, starting materials: benzyl alcohql, p-chlorophenol As Example 8, but metering of about 65 g/hour of a mixture of 128.5 g of p-chlorophenol, 108 g of benzyl alcohol and 19 mg of methanesulphonic acid (0.01 mol %). The result corresponded to that of Example 8, but 0.1% of benzyl 4-chlorophenyl ether were found in the lower product stream.

EXAMPLE 10

Reaction distillation, catalyst of sulphuric acid, starting materials: benzyl alcohol, p-chlorophenol As Example 8, but metering of about 100 g/hour of a mixture of 128.5 g of p-chlorophenol, 108 g of benzyl alcohol and 200 mg of sulphuric acid (100% strength).

The result was identical to that of Example 8, with the difference that the bottom product was obtained not in a pale yellowish- to brownish-coloured form but in an intensely green-coloured form.

EXAMPLE 11

Reaction distillation, catalyst of sulphuric acid, starting materials: benzyl alcohol, p-chlorophenol As Example 10, but 144 mg/hour of $NaHCO_3$ in 10 g of product mixture were metered in directly below the middle evaporator part.

The result was identical to that of Example 10, with the difference that the bottom product was brown-coloured and was cloudy due to precipitated sodium salt.

EXAMPLE 12

Reaction distillation, catalyst of methanesulphonic acid, starting materials: benzyl chloride, p-chlorophenol The apparatus consisted of, from the bottom upwards:
- glass flask (250 ml) with a regulated nitrogen inlet for receiving the bottom product (the main product of the reaction was obtained from this flask by being suctioned off from time to time);
- coil evaporator thermostatically controlled by oil (coil length about 1.50 m, internal diameter of the tube about 1.5 cm);
- vacuum-metallised packed column, filled with porcelain saddles 0.5 cm in size (internal diameter of the column about 2.7 cm, height of the column about 35 cm); column part thermostatically controlled by oil, filled with porcelain saddles (diameter about 2.7 cm, height about 35 cm);
- glass tube with a heated branch for metering in benzyl chloride and for recycling unreacted benzyl chloride/p-chlorophenol mixture (distillate) (diameter about 2.7 cm, height about 10 cm; 20 cm feed tube, thermostatically controlled at 200° C. with a heating tape, internal diameter 1.5 cm);
- perforated tray column thermostatically controlled by oil for thermal insulation (10 trays; liquid contents about 60 ml, height about 60 cm, internal diameter about 5 cm); glass tube with a branch for metering in p-chlorophenol/catalyst mixture (diameter about 2.7 cm, height about 10 cm);
- column part thermostatically controlled by oil, containing porcelain saddles (diameter about 2.7 cm, height about 15 cm);
- vacuum-metallised packed column containing porcelain saddles (internal diameter of the column about 2.7 cm, height about 30 cm);
- air bridge to the downwards-operated condensation part of two intensive condensers, Anschütz head, glass cap with a vacuum hose and an insulated 25 ml collecting cylinder with a tap, from which the condensate was recycled to the benzyl chloride feed at a defined metering rate.

The vacuum in the apparatus was kept constant by a magnetically controlled water pump (±1.5 mbar).

The benzyl chloride was metered in by a vacuum-tight metering pump (TELAB, PTFE minimeterer).

The p-chlorophenol/catalyst mixture was metered in by means of a heated Lewa pump with a pressure retention valve (3 bar).

The condensate was recycled using a vacuum-tight metering pump (TELAB, PTFE minimeterer).

A mixture of 1000 g of p-chlorophenol and 800 mg of methanesulphonic acid hydrate was introduced into the heated reservoir of the Lewa pump, the benzyl chloride reservoir was filled and the pressure in the apparatus was adjusted to 120 mbar. Pumping of p-chlorophenol was then started, until a clear reflux was established in the apparatus.

(Oil temperature of the lower evaporator about 250° C., oil temperature of the middle evaporator about 238° C., oil temperature of the perforated tray column about 142° C., oil temperature of the upper condenser about 60° C.).

The total liquid content of the distillation apparatus at this point in time was about 80 ml. An $N_2$ stream of 0.1 Nl/hour was introduced into the lower part of the apparatus. The benzyl chloride and p-chlorophenyl metering were adjusted to 82 ml/hour in each case. A temperature of 100 to 105° C. was established at the head of the apparatus, and a mixture of 67% by weight of benzyl chloride and 33% by weight of p-chlorophenol condensed and flowed into the reservoir of the recycling pump. This was adjusted to about 400 ml/hour and fed the condensate back into the column via the benzyl chloride feed. About 147 to 149 g of a mixture of 90% by weight of 2-benzyl-4-chlorophenol, 1% by weight of 3-benzyl-4-chlorophenol and 9% by weight of high-boiling constituents (polybenzylated phenols) per hour dripped into the bottom flask of the apparatus. The content of benzyl 4-chlorophenyl ether was less than 0.01%.

EXAMPLE 13

Reaction distillation, catalyst of methanesulphonic acid, starting materials: benzyl chloride, p-chlorophenol As Example 12, but 27 ml of benzyl chloride and 23 ml of p-chlorophenol per hour were metered in.

At 90 to 92° C., a mixture of 74% by weight of benzyl chloride and 26% by weight of p-chlorophenol condensed at the head of the apparatus. This mixture was pumped back into the reactor at a rate of 100 ml/hour. About 50 g of a mixture of 95% of 2-benzyl-4-chlorophenol, 1% of 3-benzyl-4-chlorophenol and 4% of high-boiling constituents per hour dripped into the bottom flask of the apparatus. No benzyl 4-chlorophenyl ether was detectable.

What is claimed is:

1. A process for the preparation of an o-benzylphenol substituted in the p-position, of the formula

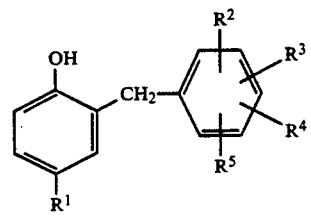

in which
R$^1$ represents halogen, hydroxyl, C$_1$-C$_{12}$-alkyl, C$_1$-C$_{12}$-alkoxy, C$_1$-C$_{12}$-alkylmercapto, C$_6$-C$_{12}$-aryl, C$_6$-C$_{12}$-aryloxy or C$_6$-C$_{12}$-arylmercapto and
R$^2$ to R$^5$ independently of one another denote hydrogen, halogen, the cyano group, C$_1$-C$_{12}$-alkyl, C$_1$-C$_{12}$-alkoxy, C$_1$-C$_{12}$-alkylmercapto, C$_6$-C$_{12}$-aryl, C$_6$-C$_{12}$-aryloxy or C$_6$-C$_{12}$-arylmercapto, and two of the radicals of R$^2$ to R$^5$ demote trimethylene, tetramethylene or the radical of a fused-on benzene ring, by reaction of a p-substituted phenol of the formula

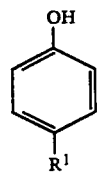

in which
R$^1$ has the abovementioned meaning, with a benzyl compound of the formula

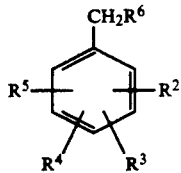

in which
R² to R⁵ have the abovementioned and
R⁶ represents halogen, $C_1-C_{12}$-alkylcarboxyl, substituted or unsubstituted phenylcarboxyl, $C_1-C_{12}$-alkyl- or phenylsulphatoxy, hydroxyl, $C_1-C_{12}$-alkoxy, substituted or unsubstituted benzyloxy or substituted or unsubstituted p-R¹-phenoxy, wherein R¹ has the abovementioned meaning,
wherein the reaction is carried out in a continuously operating distillation apparatus in the presence of at least one soluble Bronsted acid catalyst, having a $pK_1$ value of 0 to $-12$.

2. The process of claim 1, wherein the acid catalyst is a Bronsted acid.

3. The process of claim 1, wherein an excess of phenol is maintained inside the reactor.

4. The process of claim 1, wherein the distillation apparatus has, above the zone for discharge of the product an additional heat exchanger for evaporation of the majority of the internal excess of phenol.

5. The process of claim 4, wherein the additional heat exchanger is in the central, region of the distillation apparatus.

6. The process of claim 1, wherein the distillation apparatus has, in the upper region, an additional heat exchanger for precipitation of the majority of the internal excess of phenol.

7. The process of claim 6, wherein, in the addition heat exchanger for precipitation of the phenol, the energy is recovered.

8. The process of claim 1, wherein an additional azeotrope-forming agent is employed for effective separation of the educts from the highly volatile reaction product.

9. The process of claim 1, wherein one of the catalytically active acids employed has a $pK_a$ of $<0$.

10. The process of claim 9, wherein one of the catalytically active acids employed has a $pK_a$ of $<-1$.

11. The process of claim 10, wherein one of the catalytically active acids employed has a $pK_a$ of $<-2$.

12. The process of claim 2, wherein one of the catalytically active acids is toluene-sulphonic acid, benzenesulphonic acid, sulphuric acid or methanesulphonic acid.

13. The process of claim 12, wherein one of the catalytically active acids is sulphuric acid or methanesulphonic acid.

14. The process of claim 1, wherein the amount of acid in relation to the benzyl equivalent employed is between 10 and 0.001 mol%.

15. The process of claim 14, wherein the amount of acid is between 5 and 0.002 mol%.

16. The process of claim 15, wherein the amount of acid is between 1 and 0.004 mol%.

17. The process of claim 1, which is carried out in a pressure range from 1 mbar to 10 bar.

18. The process of claim 1, wherein in the reaction region of the column, the ratio of the phenol component to the sum of the product component and unreacted benzyl equivalents at each point is greater than 2.

19. The process of claim 18, wherein the ratio of the phenol component of the sum of the product component an unreacted benzyl equivalents at each point is greater than 4.

20. The process of claim 19, wherein the ratio of the phenol component to the sum of the product component an unreacted benzyl equivalents at each point is greater than 8.

* * * * *

UNITED STATES PATENT AND TRADEMARK OFFICE
CERTIFICATE OF CORRECTION

PATENT NO. : 5,258,554
DATED : November 2, 1993
INVENTOR(S) : Langer, et al.

It is certified that error appears in the above-identified patent and that said Letters Patent is hereby corrected as shown below:

Title Page      U.S. PATENT DOCUMENTS: After " Buysch et al. ... " insert -- 568/744 --

Col. 14, line 53      Delete " demote " and substitute -- denote --

Col. 15, line 20      Delete "$pK_1$ " and substitute -- $pK_a$ --

Col. 16, line 13      Delete " Or " and substitute -- or --

Signed and Sealed this

First Day of June, 1999

*Attest:*

Q. TODD DICKINSON

*Attesting Officer*      *Acting Commissioner of Patents and Trademarks*